United States Patent
Zumbrum et al.

(10) Patent No.: US 12,234,932 B2
(45) Date of Patent: *Feb. 25, 2025

(54) TUBE ORGANIZER ASSEMBLY

(71) Applicant: Sartorius Stedim North America Inc., Bohemia, NY (US)

(72) Inventors: Michael Zumbrum, New Oxford, PA (US); William Kimmick, Mechanicsburg, PA (US); Kevin Perdue, Havre de Grace, MD (US)

(73) Assignee: Sartorius Stedim North America Inc., Bohemia, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/223,256

(22) Filed: Jul. 18, 2023

(65) Prior Publication Data
US 2023/0358343 A1    Nov. 9, 2023

Related U.S. Application Data

(63) Continuation of application No. 17/498,830, filed on Oct. 12, 2021, now Pat. No. 11,746,929.

(51) Int. Cl.
*F16L 3/22* (2006.01)
*F16L 3/02* (2006.01)

(52) U.S. Cl.
CPC ............. *F16L 3/222* (2013.01); *F16L 3/02* (2013.01)

(58) Field of Classification Search
CPC ... F16L 3/222; F16L 3/02; F16L 3/223; F16L 3/233; F16L 3/137; F16L 3/227; F16L 3/2235; F16L 3/22; F16L 3/237
See application file for complete search history.

(56) References Cited

U.S. PATENT DOCUMENTS

| | | | |
|---|---|---|---|
| 2,489,119 A | 11/1949 | Burns et al. | |
| 3,649,998 A * | 3/1972 | Fiorentino | F16B 2/08 403/188 |

(Continued)

FOREIGN PATENT DOCUMENTS

| | | |
|---|---|---|
| CA | 2913956 A1 | 12/2014 |
| CN | 1270904 A | 10/2000 |

(Continued)

OTHER PUBLICATIONS

Electronic Goldmine—G20062 Cable Ties for Tube Mounting, retrieved from https://theelectronicgoldmine.com/products/g20062?_pos=1&_sid=45283698c&_ss=r, known as least as early as Mar. 26, 2021, 2 pages.

(Continued)

*Primary Examiner* — Christopher Garft
(74) *Attorney, Agent, or Firm* — Womble Bond Dickinson (US) LLP

(57) ABSTRACT

An organizer assembly including a belt and a ribbon. The ribbon has a first clamp member, a second clamp member, and a first carrier portion. The first clamp member is configured to receive a conduit or a support to fix the conduit or the support relative to the ribbon. The belt includes an elongated body that is slidably received in the first carrier portion. The organizer assembly may include one or more adapters that are received in a respective clamp member of the ribbon and configured to receive a conduit or a support to fix the conduit or support relative to the ribbon.

17 Claims, 8 Drawing Sheets

(56) References Cited

U.S. PATENT DOCUMENTS

| | | | |
|---|---|---|---|
| 4,639,980 A | | 2/1987 | Peterson |
| 5,289,961 A | | 3/1994 | Levitt et al. |
| 5,437,399 A | * | 8/1995 | Levitt .................. A45F 5/02 |
| | | | 401/6 |
| 5,703,330 A | | 12/1997 | Kujawski |
| 5,749,504 A | * | 5/1998 | Bieker .................. A45F 3/00 |
| | | | 224/267 |
| 6,330,989 B1 | | 12/2001 | Okamoto |
| 7,527,012 B2 | | 5/2009 | Kutny Splaine |
| 8,851,430 B2 | * | 10/2014 | Mulzer ................ B65D 85/42 |
| | | | 248/65 |
| D747,276 S | | 1/2016 | Rodrigue |
| 9,622,941 B2 | | 4/2017 | Sharpe et al. |
| 9,791,102 B2 | * | 10/2017 | Moreau .................. F16M 13/04 |
| 10,433,926 B2 | | 10/2019 | Recanati et al. |
| 10,857,331 B2 | | 12/2020 | Moudy |
| 10,865,912 B2 | | 12/2020 | Bechtold |
| 11,746,929 B2 | | 9/2023 | Zumbrum et al. |
| 2001/0030271 A1 | * | 10/2001 | Weesner ............... A61M 5/008 |
| | | | 248/230.8 |
| 2006/0113432 A1 | | 6/2006 | Driskell |
| 2011/0316274 A1 | | 12/2011 | Gronlund et al. |
| 2013/0233597 A1 | | 9/2013 | Suiter |
| 2014/0259620 A1 | | 9/2014 | Hicks et al. |
| 2015/0224009 A1 | * | 8/2015 | Cedrone ................ F16M 13/04 |
| | | | 24/316 |
| 2016/0114103 A1 | | 4/2016 | Burke |
| 2020/0103053 A1 | * | 4/2020 | Weber .................... H02G 3/32 |
| 2020/0185899 A1 | * | 6/2020 | Leng ........................ F16L 3/13 |
| 2020/0244058 A1 | * | 7/2020 | Crounse ................ F16L 3/1091 |

FOREIGN PATENT DOCUMENTS

| | | |
|---|---|---|
| DE | 60031029 T2 | 3/2007 |
| EP | 1044871 A2 | 10/2000 |
| EP | 3003424 A1 | 4/2016 |
| TW | 450911 B | 8/2001 |
| WO | 2014190424 A1 | 12/2014 |
| WO | 2023062535 A1 | 4/2023 |

OTHER PUBLICATIONS

International Search Report for pending PCT Application PCT/IB/2022/059743 dated Dec. 19, 2022, 3 pages.

International Preliminary Report on Patentability and Written Opinion for Pending PCT Application PCT/IB2022/059743, issued Apr. 25, 2024, 8 pages.

* cited by examiner

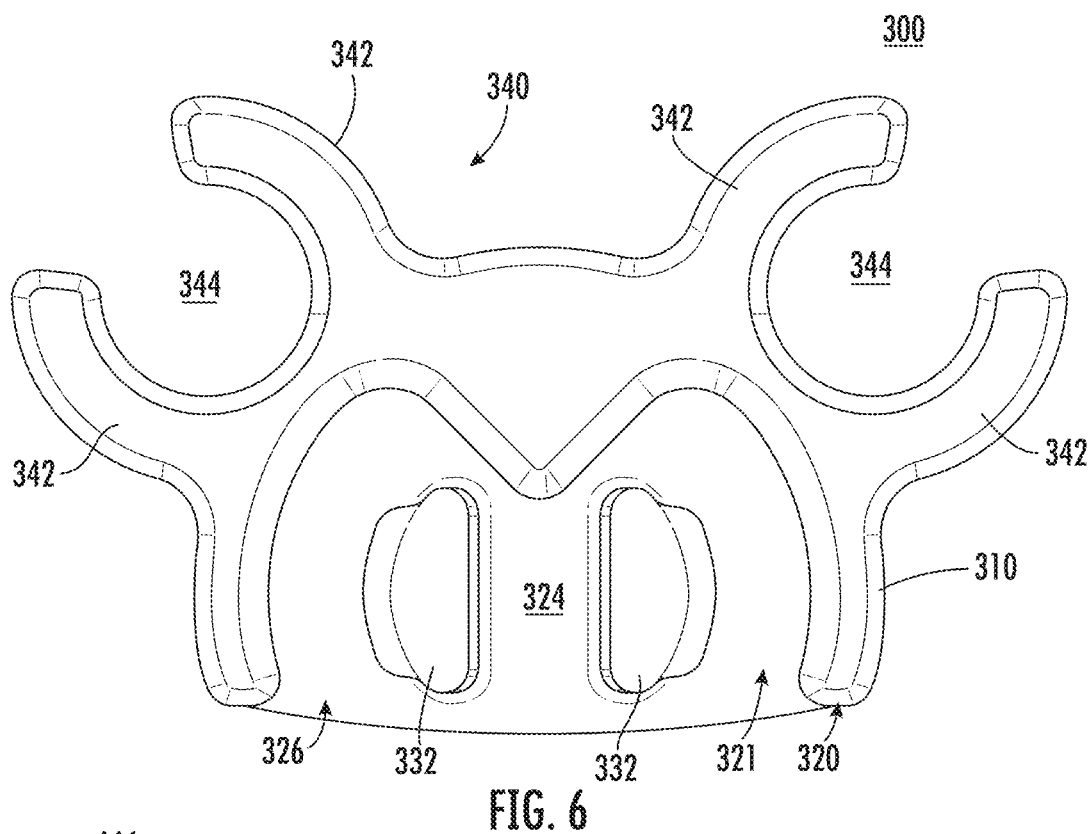
FIG. 6
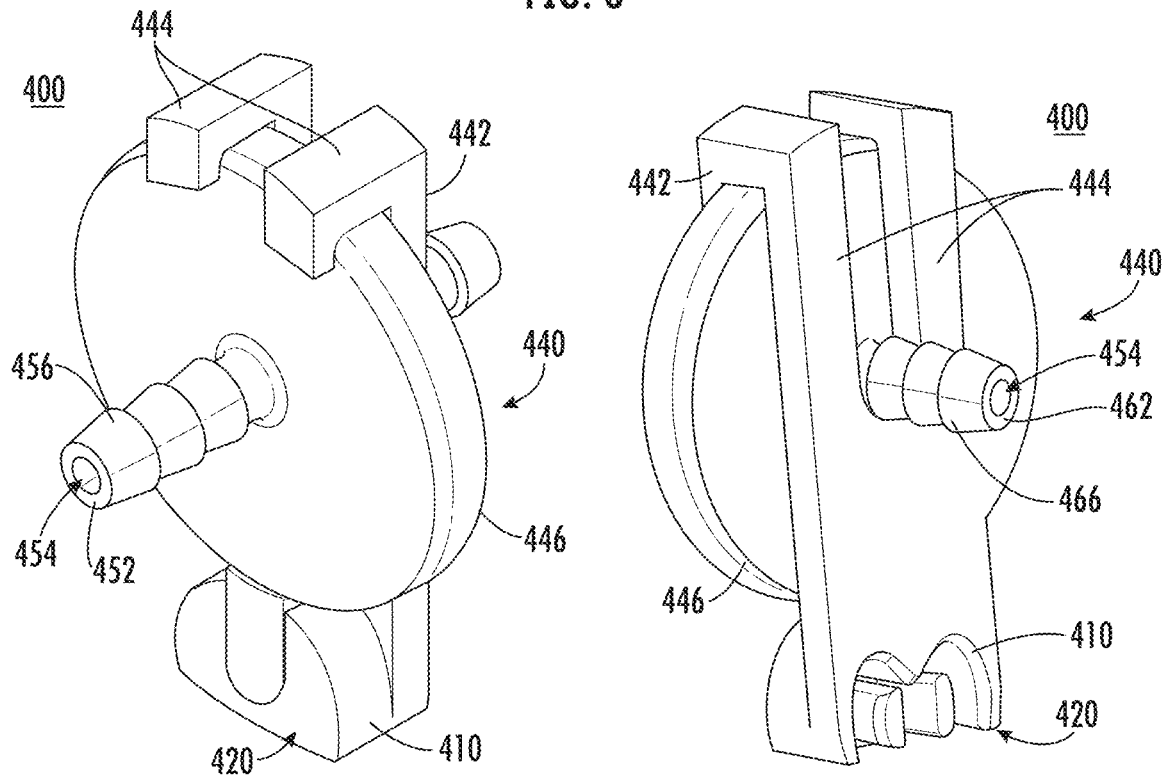
FIG. 7
FIG. 8

TUBE ORGANIZER ASSEMBLY

CROSS-REFERENCE TO RELATED APPLICATION

This application is a continuation of U.S. patent application Ser. No. 17/498,830, filed Oct. 12, 2021, the entire contents of which are hereby incorporated by reference in its entirety.

BACKGROUND

1. Technical Field

The present disclosure relates to tube organization and, more specifically, to a customizable tube organizer assembly.

2. Discussion of Related Art

Biopharmaceutical and pharmaceutical drug developers and manufactures often develop and manufacture products in a fluid form. These products must be handled with care to maintain an aseptic environment and avoid contamination. Drugs developed and produced by biopharmaceutical and pharmaceutical companies are often produced through a multitude of steps that may require transfer of the fluids through conduits for purposes of sampling, packaging, mixing, separating, or passing between stations for various steps of the manufacturing process.

The manufacturing and testing processes required by biopharmaceutical and pharmaceutical companies require significant opportunities for fluid transfer. Each occurrence of fluid transfer that relies upon separate containers, conduits, or components to leave the source and arrive at the destination creates an opportunity for leaks to occur or contamination to enter.

Often, several fluid pathways are required to enter or exit various containers. Traditionally, the fluid pathways have all been maintained independent of one another, requiring a large number of separate fittings between conduits and requiring a significant amount of space to accommodate the fittings for each fluid pathway separately. In addition, sequential filling of multiple containers, one container at a time, consumed significant amounts of time and resources in a cleanroom environment and at considerable cost.

The present disclosure describes improvements to maintain aseptic environments and avoid contamination during fluid transfer by increasing organization of fluid pathways, reducing space requirements, and simplifying assembly to produce a reliable low-cost fluid transfer assembly. Because fluid transfer assemblies are often rendered aseptic and are intended for a single use, maintaining a low cost through reducing assembly steps can provide significant advantages.

SUMMARY

This disclosure relates generally to an organizer assembly that is configured to secure a plurality of conduits to a vessel.

In an embodiment of the present disclosure, an organizer assembly that includes a belt and a ribbon. The belt has an elongated body. The ribbon includes a first clamp member, a second clamp member, and a first carrier portion. The first carrier portion slidably receives the elongated body of the belt therethrough. The first clamp member is configured to receive a conduit or a support to fix the conduit or the support relative to the ribbon. The belt is configured to secure the ribbon about a vessel.

In embodiments, the ribbon is formed of a resilient material. The ribbon is formed of a polymeric material. The polymeric material may be a cross-linked polyurethane (e.g., silicone) or a polyamide (e.g., nylon). The belt may be formed of a thermoplastic material such as a polyamide including, but not limited to, nylon or a metal. The first clamp member and the second clamp member may each include a pair of opposed fingers that define a holder therebetween.

In some embodiments, the first carrier portion is aligned with the first clamp member. The ribbon may include a band that interconnects the first clamp member, the second clamp member, and the first carrier portion. The ribbon may be monolithically formed.

In certain embodiments, the organizer assembly includes an adapter that has a receiver section and a mount section. The receiver section may be configured to receive the first clamp member therein to fix the adapter to the ribbon. The first clamp member may be configured to receive the conduit or the support extending in a first holder direction. The mount section may define a passage that is sized and dimensioned to receive at least one conduit or support therein. The passage may be defined by the mount section that is configured to receive the at least one conduit or support that extend in a second passage direction that is perpendicular to the first holder direction.

In particular embodiments, the mount section of the adapter includes a first pair of fingers and a second pair of fingers. The first pair of fingers may define a first passage and the second pair of fingers may define a second passage. The first passage and the second passage may each be configured to receive a conduit or a support. The first passage and the second passage may extend in a second passage direction that is perpendicular to the first holder direction.

In another embodiment of the present disclosure, a method of securing a conduit to a vessel includes selecting a first ribbon that includes a first clamp member, a second clamp member, and a first carrier portion, threading an elongated body of a belt through a tunnel of the first carrier portion, wrapping the elongated body about a portion of a vessel, securing the belt about the portion of the vessel such that the first ribbon is secured to the portion of the vessel, and securing a conduit to the first clamp member of the first ribbon.

In embodiments, selecting the first ribbon includes trimming the first ribbon such that a third clamp member is separated from the first clamp member and the second clamp member.

In some embodiments, the method includes selecting a second ribbon that includes a first clamp member and a second carrier portion. Threading the elongated body of the belt may include threading the elongated body through a tunnel of the second carrier portion. Securing the belt around the portion of the vessel may include serving the second ribbon to the portion of the vessel. The method may include securing another conduit to the fourth clamp member.

In particular embodiments, the method includes fixing an adapter to the first clamp member. Securing the conduit to the first clamp member may include securing the conduit to a mount section of the adapter. The method may include securing another conduit to the mount section of the adapter.

In another embodiment of the present disclosure, an organizer assembly includes a belt and a first ribbon. The belt includes an elongated body. The first ribbon includes a plurality of clamp members and a plurality of carrier portions. Each carrier portion of the plurality of carrier portions of the first ribbon is configured to slidably receive the elongated body of the belt therethrough. Each clamp member of the plurality of clamp members of the first ribbon is configured to selectively receive a conduit or a support to fix the conduit or the support relative to the ribbon. The belt is configured to secure the first ribbon about a vessel.

In embodiments, the organizer assembly includes a second ribbon that has a plurality of clamp members and a plurality of carrier portions. Each carrier portion of the plurality of carrier portions of the second ribbon may be configured to slidably receive the elongated body of the belt therethrough. Each clamp member of the plurality of clamp members of the second ribbon may be configured to selectively receive a conduit or a support to fix the conduit or the support relative to the ribbon. The belt may be configured to secure the second ribbon about a vessel.

In some embodiments, the plurality of clamp members of the first ribbon may include a first number of clamp members and the plurality of clamp members of the second ribbon may include a second number of clamp members with the first number of clamp members being different from the second number of clamp members.

In certain embodiments, the first ribbon may be of monolithic construction. The ribbon may be formed of a resilient material. In particular embodiments, the ribbon comprises a polymeric material including thermosets or thermoplastics, a metal, or combinations thereof. The polymeric material may be a polyimide or a cross-linked polyurethane including, but not limited to, silicone or nylon. The belt may comprise of a thermoplastic polymer such as a polyamide including, but not limited to, nylon. In some embodiments, the belt comprises a metal.

In embodiments, the belt may include a head and the elongated body may include a plurality of teeth. The head may include a channel that is defined therethrough and a pawl that extends into the channel. The elongated body may be configured to pass through the channel with the pawl selectively engaging a tooth of the plurality of teeth to prevent the elongated body from being retracted through the channel of the head.

In some embodiments, each clamp member of the first clamp member and the second clamp member each include a pair of opposed fingers that define a holder therebetween. The holder may be sized and dimensioned to secure a conduit or support therein. Each finger of the pair of opposed fingers may be self-biased towards the opposed finger.

In certain embodiments, each carrier portion of the plurality of carrier portions of the first ribbon is aligned with a clamp member of the plurality of clamp members of the first ribbon. The organizer assembly may include an adapter having a receiver section and a mount section. The receiver section may be received on a clamp member of the plurality of clamp members of the first ribbon to fix the adapter to the ribbon. The clamp members of the plurality of clamp members of the first ribbon are each configured to receive a conduit or a support extending in a first holder direction. The mount section of the adapter may define a passage sized and dimensioned to receive at least one conduit or support therein. The passage may be defined by the mount section is configured to receive the at least one conduit or support extending in a second passage direction that is perpendicular to the first holder direction. The mount section of the adapter may include a first pair of fingers and second pair of fingers. The first pair of fingers may define a first passage and a second pair of fingers may define a second passage. The first passage and the second passage are each configured to receive a conduit or a support. The passage may be defined by the mount section that is configured to receive the at least one conduit or support extending in a second passage direction that is perpendicular to the first holder direction. The mount section of the adapter may include a first pair of fingers and a second pair of fingers. The first pair of fingers that define a first passage and the second pair of fingers define a second passage. The first passage and the second passage are each configured to receive a conduit or a support.

In particular embodiments, the mount section may include a first connector. The first connector may define a lumen therethrough. The first connector is configured to receive a conduit thereabout such that the conduit is in fluid communication with the lumen. The mount section may include a second connector. The second connector may be configured to receive a conduit thereabout such that the conduit is in fluid communication with the lumen. The lumen and the passage may be coaxially aligned and extend in a second passage direction that is parallel to the first holder direction.

In another embodiment of the present disclosure, an organizer assembly includes a ribbon that has a first clamp member and a second clamp member that are interconnected with a bond. The first clamp member is configured to receive a conduit or a support to fix the conduit or the support relative to the ribbon. The ribbon comprises a first end portion and a second end portion that is opposite the first end portion. The first end portion includes a first closure and the second end portion includes a second closure. The first closure and the second closure are engageable with one another to secure the ribbon about a vessel.

In embodiments, the ribbon comprises a polymeric material that may be a thermoset material or a thermoplastic material. The ribbon may comprise a metallic material. The ribbon may be of monolithic construction.

In some embodiments, the organizer assembly may include an adapter having a receiver section and a mount section. The receiver section may be configured to receive the first clamp member therein to fix the adapter to the ribbon. The first clamp member may be configured to receive the conduit or the support in a first holder direction. The mount section may define a passage that is sized and dimensioned to receive at least one conduit or support therein. The passage may be defined by the mount section and may be configured to receive the at least one conduit or support extending in a second passage direction that is perpendicular to the first holder direction. The mount section of the adapter may include a first pair of fingers and a second pair of fingers. The first pair of fingers ma define a first passage and a second pair of fingers that define a second passage. The first passage and the second passage may each be configured to receive a conduit or a support.

In certain embodiments, the first closure may include a first rack and the second closure may include a second rack. The first and second racks may be configured to ratchet over one another as the first end portion is urged over the second end portion and to prevent the first end portion from withdrawing from over the second end portion.

In particular embodiments, the first closure includes a pocket defined therethrough and the second closure includes a hook. The pocket may be sized and dimensioned to receive the hook such that the first end portion is secured to the second end portion.

Further, to the extent consistent, any of the embodiments or aspects described herein may be used in conjunction with any or all of the other embodiments or aspects described herein.

BRIEF DESCRIPTION OF THE DRAWINGS

Various aspects of the present disclosure are described herein below with reference to the drawings, which are incorporated in and constitute a part of this specification, wherein:

FIG. 6 is a back view of another example adapter provided in accordance with the present disclosure;

FIG. 7 is a front perspective view of another example adapter provided in accordance with the present disclosure;

FIG. 8 is a back perspective view of the adapter of FIG. 7;

DETAILED DESCRIPTION

Figure 1:
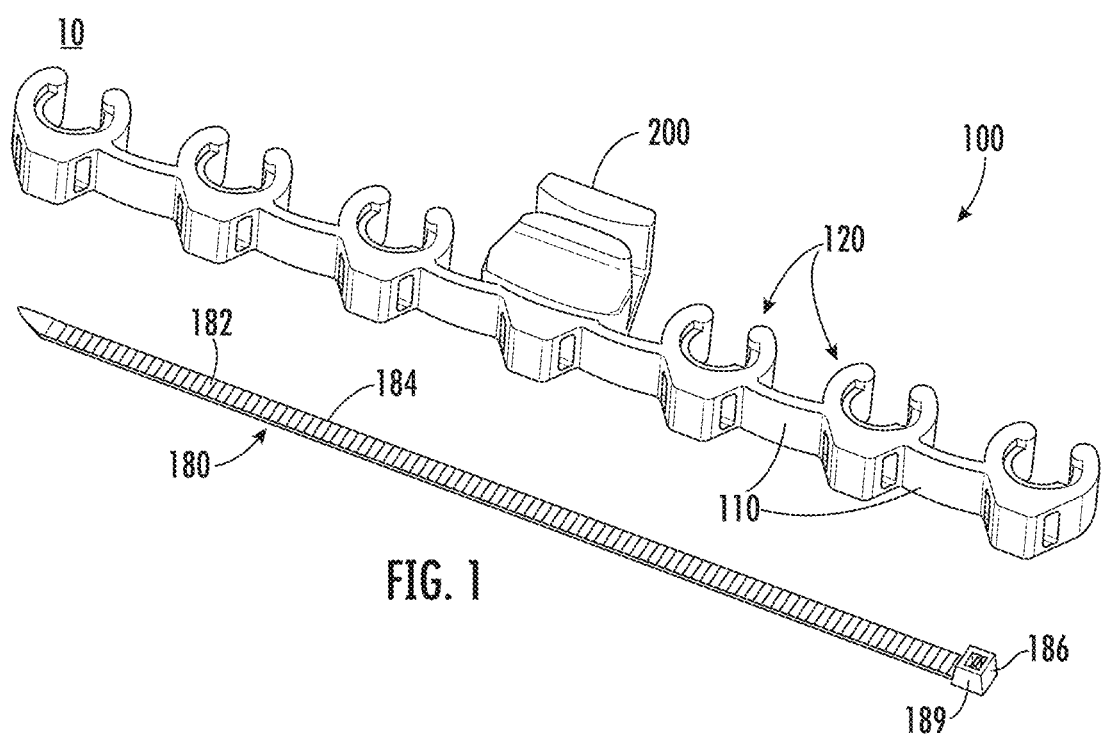
FIG. 1 is a top perspective view of an example tube organizer assembly provided in accordance with the present disclosure.

The present disclosure will now be described more fully hereinafter with reference to example embodiments thereof with reference to the drawings in which like reference numerals designate identical or corresponding elements in each of the several views. These example embodiments are described so that this disclosure will be thorough and complete, and will fully convey the scope of the disclosure to those skilled in the art. Features from one embodiment or aspect can be combined with features from any other embodiment or aspect in any appropriate combination. For example, any individual or collective features of method aspects or embodiments can be applied to apparatus, product, or component aspects or embodiments and vice versa. The disclosure may be embodied in many different forms and should not be construed as limited to the embodiments set forth herein; rather, these embodiments are provided so that this disclosure will satisfy applicable legal requirements. As used in the specification and the appended claims, the singular forms "a," "an," "the," and the like include plural referents unless the context clearly dictates otherwise. In addition, while reference may be made herein to quantitative measures, values, geometric relationships or the like, unless otherwise stated, any one or more if not all of these may be absolute or approximate to account for acceptable variations that may occur, such as those due to manufacturing or engineering tolerances or the like.

Referring now to FIG. 1, an organizer assembly is provided in accordance with an embodiment of the present disclosure and is referred to as organizer assembly 10. The organizer assembly 10 includes a ribbon 100 and a belt 180. The ribbon 100 includes clamp members 120 that may be interconnected by a band 110. The band 110 aligns the clamp members 120 and spaces the clamp members 120 apart from one another.

Figure 2:
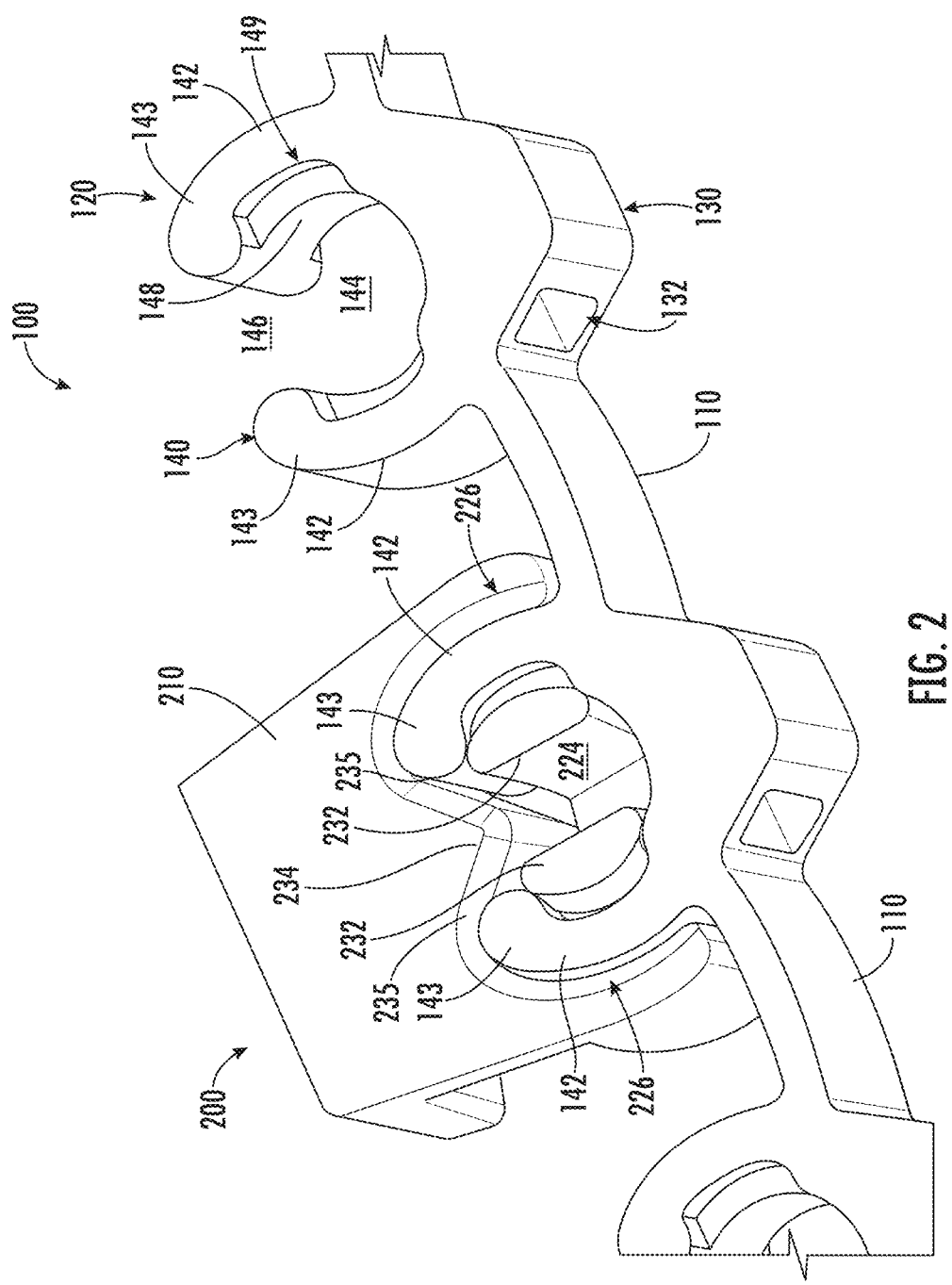
FIG. 2 is an enlarged, bottom perspective view of a portion of the tube organizer assembly of FIG. 1.

With additional reference to FIG. 2, the clamp members 120 include a carrier portion 130 and a catch portion 140. The carrier portion 130 defines a tunnel 132 that slidably receives the belt 180 therethrough. As shown, the carrier portions 130 are aligned with the clamp members 120. In some embodiments, the carrier portions 130 may be offset with respect to the clamp members 120. In particular embodiments, a carrier portion 130 is disposed between two clamp members 120.

The catch portion 140 includes two fingers 142 that extend away from the carrier portion 130 to define a holder 144 such that the holder 144 passes between the fingers 142. The finger 142 may define a gate 146 that provides access to the holder 144. The gate 146 may be positioned between tips 143 of the fingers 142 to allow access to the holder 144. The gate 146 may partially close the holder 144 to prevent an object disposed within the holder 144 from unintentionally being released from the holder 144. The fingers 142 may be resilient to allow an object to be pressed through the gate 146 and into the holder 144. The fingers 142 may be self-biased towards one another to provide a gripping force to objects disposed within the holder 144 as detailed below.

The fingers 142 may include rib 148 that extends on an interior surface of the finger 142 facing the holder 144. The rib 148 may be centrally located along the interior surface of the finger 142 such that a shelf 149 is defined on either side of the rib 148 with the inside surface of the finger 142. The rib 148 may be configured to engage an object passing through the holder 146 to retain the object relative to the clamp member 120.

Continuing to refer to FIGS. 1 and 2, the organizer assembly 10 may include one or more adapters 200 attached to the ribbon 100. The adapters 200 may be disposed about the neck 22 of the flask 20 (FIG. 9) to support or position tubes or conduits relative to the flask 20 separate from the holders 144. For example, the adapter 200 is attached to a holder 144 of the ribbon 100 to support a tube or conduit extending in a direction orthogonal to the holder 144 to which the adapter 200 is attached. The organizer assembly 10 may include no adapters 200 or may include a plurality of adapters 200 depending on the application of the organizer assembly 10. In some embodiments, the organizer assembly 10 may include more than one ribbon 100. For example, an organizer assembly 10 may include a range of 1 to 20 ribbons 100. In such embodiments, the ribbons 100 of a particular organizer assembly 10 may have the same number of clamp members 120 or may have a different number of clamp members 120. In particular embodiments, an organizer assembly 10 may have three ribbons 100 on a single belt 180 with a first ribbon 100 having a single clamp member 120, a second ribbon having four clamp members 120, and a third ribbon 100 having three clamp members 120. The ribbons 100 may be selected for a variety of reasons including, but not limited to, the number of clamp members 120, the spacing of the clamp members 120 along the ribbon 100 (e.g., the length of the bands 110 between the clamp members 120), the orientation of holders 144 on the ribbon 100, or the size of the holders 144 on the ribbon 100.

Figure 3:
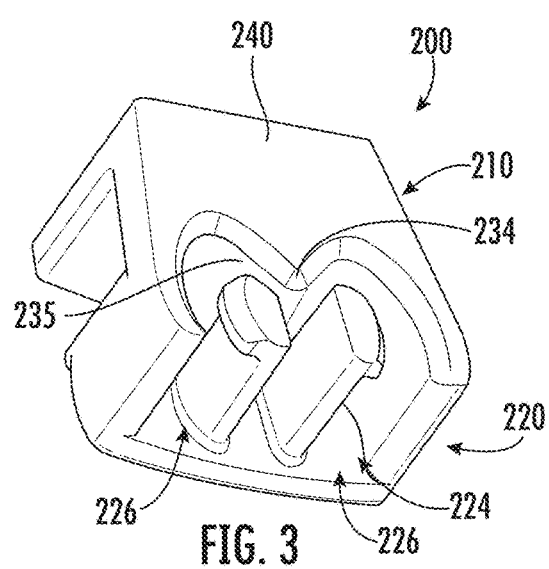
FIG. 3 is a front perspective view of an adapter of the tube organizer assembly of FIG. 1.
Figure 4:
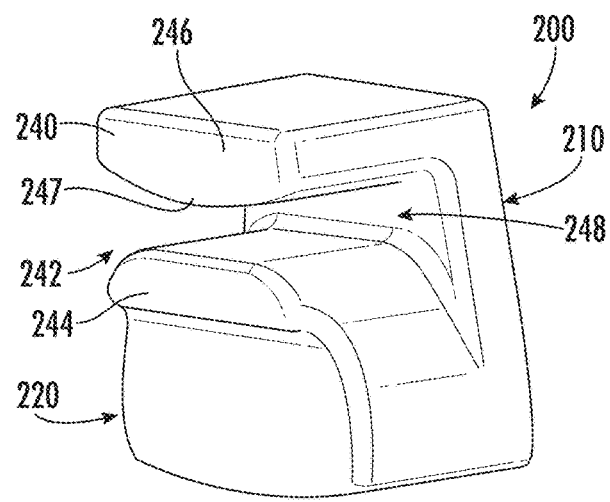
FIG. 4 is a back perspective view of the adapter of FIG. 3.
Figure 5:
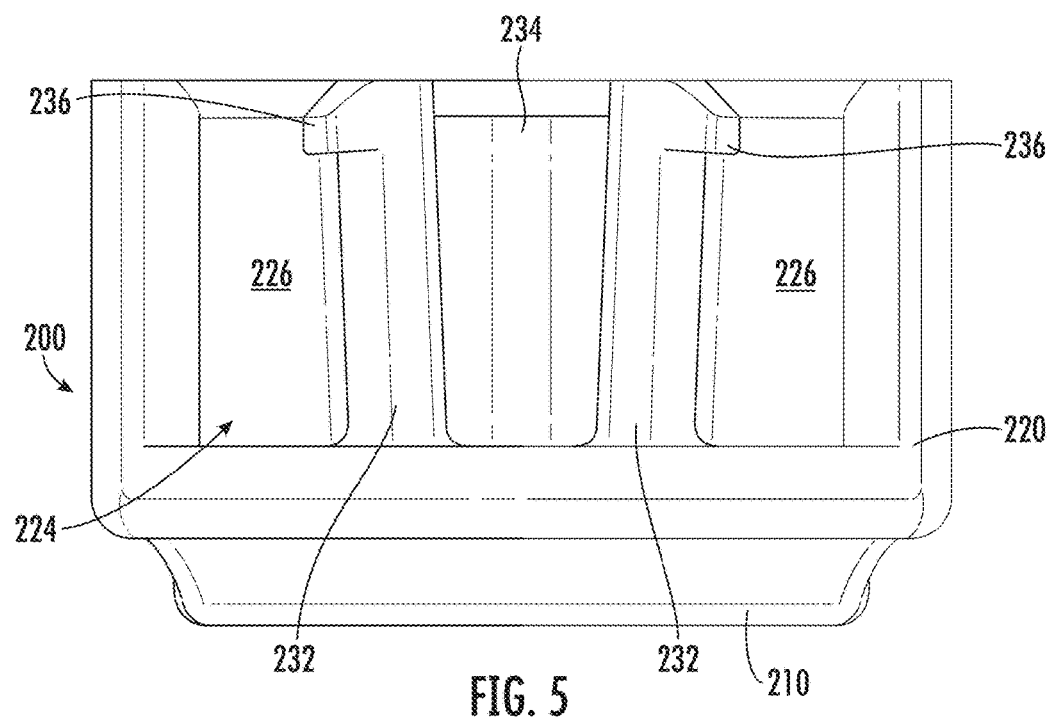
FIG. 5 is a bottom view of the adapter of FIG. 3.

Referring now to FIGS. 3-5, the adapter 200 is described in accordance with an embodiment of the present disclosure with reference to the ribbon 100 of FIGS. 1 and 2. The adapter 200 includes a body 210 having a receiver section 220 and a mount section 240.

The receiver section 220 defines a cavity 224 that is sized and shaped to receive a clamp member 120 of the ribbon 100. The cavity 224 includes grips 232 that extend into the cavity 224 such that a sleeve 226 of the cavity 224 is formed on a side of the grips 232. The sleeves 226 of the cavity 224 are sized and dimensioned to receive a pair of opposed fingers 142 such that the grips 232 are disposed in the holder 144 defined between the pair of opposed fingers 142. In some embodiments, the grips 232 form a single member such that the single grip substantially fills the holder 144. The grips 232 may include a bridge 234 that extends through the gate 146 defined between the tips 143 of the fingers 142. The bridge 234 may have a width, as measured as the distance between the fingers 142, that is less than the width of the remainder of the grip 232. The grips 232 may include pinch points or recesses 235 that define the bridge 234 that are configured to receive the tips 143 of the fingers 142.

The grips 232 may be sized and dimensioned to fill the holder 144 defined between the fingers 142 such that the fingers 142 are moved apart from one another such that the biasing of the fingers 142 towards one another secures the grips 232 within the holder 144 such that the body 210 of the adapter 200 is secured to the ribbon 100. The grips 232 may be slightly larger than the holder 144 such that the fingers 142 are urged apart from one another to increase a gripping force on the grip 232. The size of the grips 232 being slightly larger than the holder 144 may also account for an increase in the size of the holder 144 due to deformation of the holder 144 as a result of the ribbon 100 being secured about a vessel or support, e.g., a neck of a flask.

The grips 232 may include a ledge 236 that extends from one end of the respective grip 232 to partially close the respective sleeve 226. The ledge 236 may be configured to be received in a shelf 149 of a finger 142 to retain the finger 142 within the cavity 224.

The tips 143 of the fingers 142 may engage or be adjacent the bridge 234 such that retraction of the fingers 142 from the sleeves 226 requires a force to urge the fingers 142 apart from one another. This force may further secure the body 210 of the adapter 200 to the ribbon 100.

The mount section 240 of the adapter 200 includes a mount 242 that receives an object to maintain the object in a substantially fixed relationship with the adapter 200 and thus, the ribbon 100. The mount 242 may allow for the tube organizer assembly 10 to fix objects to the ribbon 100 that would not be securable directly in the holders 144 of the ribbon 100. Additionally or alternatively, the mount 242 may allow for securement of objects at a variety of orientations relative to the ribbon 100.

With particular reference to FIG. 4, the mount 242 defines a passage 248 that is defined to pass through the body 210 such that an object received in the passage 248 is orientated to be orthogonal to a holder 144 to which the adapter 200 is secured. The mount 242 includes a first wall 244 and a second wall 246 that define the passage 248 therebetween. As shown, the passage 248 orientated such that the passage 248 extends in a direction substantially parallel to a tangent of the ribbon 100 where the clamp member 182 is defined on the ribbon 100. One of the first wall 244 or the second wall 246 may include an arcuate segment 247 such that a center of the respective wall 244, 246 is closer to the opposing wall 244, 246 than the ends of the respective walls 244, 246. The arcuate segment 247 of the respective wall 244, 246 may engage an object disposed within the passage 248 to retain or secure the object in the passage 248. The object may be retained in the passage 248 by friction between the respective walls 244, 246. The walls 244, 246 and/or the arcuate segment 247 may deform an outer surface of the object to secure the object within the passage 248. In some embodiments, the object may be a conduit and the deformation of the conduit may be slight such that an internal lumen of the conduit is not affected by the deformation resulting from the engagement of the arcuate segment 247 and the object.

Referring now to FIG. 6, another adapter 300 is provided in accordance with the present disclosure. The adapter 300 includes a body 310 having a receiver section 320 and a mount section 340. The receiver section 320 of the adapter 300 is similar to the receiver section 220 of the adapter 200 detailed above with similar elements represented with similar labels with a "3" replacing the preceding "2". As such the elements of the receiver section 320 will not be detailed herein for brevity.

The mount section 340 includes two pairs of fingers 342 with each pair of fingers 342 defining a respective holder 344 therebetween. As shown, the holders 344 may be smaller than a holder, e.g., holder 144, configured to receive the grips 332 of the receiver section 320. In some embodiments the holders 344 may be sized and dimensioned to be the same size as the holder receiving the grips 332 or may be larger than the holder receiving the grips 322. In some embodiments, the holders 344 are sized and dimensioned to be the same as one another, and in other embodiments, the holders 344 may be sized differently. The pairs of fingers 342 may allow for the securement of conduits or other elements to the adapter 300 having a diameter different than a conduit or other element receivable in the holder 144 received within the receiver section 320. As shown, the mount section 340 includes two pairs of fingers 342; however, in some embodiments, the mount section 340 includes a single pair of fingers 342 or includes three pairs of fingers 342.

The adapter 300 may be used to secure conduits or other elements to a holder 140 having a different diameter than the holder 144. The mount section 340 may allow for securement of multiple conduits or other elements to a single holder 140 of the ribbon 100. The mount section 340 may allow for securement of conduits or other elements to a holder 140 spaced apart or separated a distance from the holder 140.

Referring now to FIGS. 7 and 8, another adapter 400 is provided in accordance with the present disclosure. The adapter 400 includes a body 410 having a receiver section 420 and a mount section 440. The receiver section 420 of the adapter 400 is similar to the receiver section 220 of the adapter 200 detailed above with similar elements represented with similar labels with a "4" replacing the preceding "2". As such the elements of the receiver section 420 will not be detailed herein for brevity.

The mount section 440 includes a support 442 and a vent/filter 446. The support 442 extends from the receiver section 420 in a direction away from a ribbon supporting the mount section 440, e.g., to support the vent/filter 446 relative to the receiver section 420. The support 442 may be in the form of one or more beams 444 that receive or are formed with a housing of the vent/filter 446. The housing of the vent/filter 446 is received or formed with the support 442. The mount section 440 includes a first connector 452 and a second connector 462. The first connector 452 and the second connector 462 form a lumen 454 that extends between the first connector 452 and the second connector 462 and through the vent/filter 446. The first connector 452 includes one or more barbs 456 on an outer surface of the connector 452 and the second connector 462 includes one or more barbs 466 on an outer surface of the connector 462. The barbs 456, 466 are configured to secure a conduit to the respective connector 452, 462 such that the conduit is fluidly coupled to the conduit received on the other connector 452, 462. The respective connector 452, 462 may include a single barb 456, 466 or multiple barbs 456, 466 to secure a conduit to the connector 452, 462. In some embodiments, the connectors 452, 462 may include other retention mechanisms configured to secure a conduit to the adapter 400. In certain embodiments, the first connector 452 and/or the second connector 462 include an aseptic connector/disconnector to aseptically secure a conduit to the respective connector 452, 462.

The first connector 452 has a first diameter and the second connector 462 has a second diameter. The first diameter may be smaller than, equal to, or larger than the second diameter. In embodiments, where the first diameter is different from the second diameter, the adapter 400 may be used to fluidly couple to conduits having different diameters.

The adapter 400 may be used to secure conduits or other elements to a holder 140 having a different diameter than the holder 144. The mount section 340 may allow for securement of conduits or other elements to a holder 140 spaced apart or separated a distance from the holder 140.

Referring briefly back to FIG. 1, the belt 180 may be a cable tie that is sized and dimensioned to extend through the tunnels 132 of the clamp members 120. The belt 180 includes an elongated body 182 and a head 186. The elongated body 182 has a plurality of teeth 184 that extend from one side of the elongated body 182. The head 186 defines a channel 188 and a locking pawl 189. The elongated body 182 is configured to pass through the channel 188 of the head 186 with the locking pawl 189 ratcheting along the teeth 184 such that the elongated body 182 is prevented from retracting through the head 186.

Figure 9:
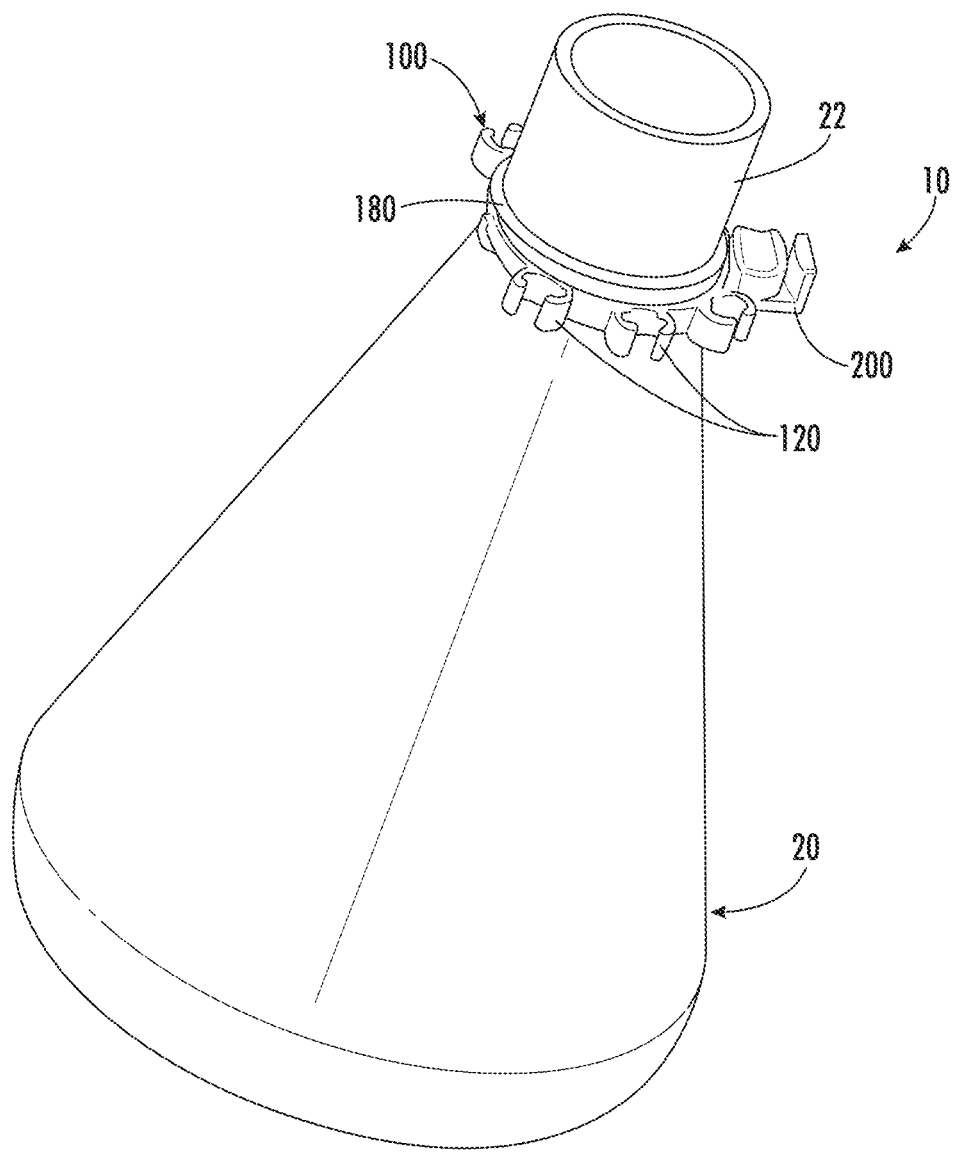
FIG. 9 is a perspective view of the tube organizer assembly of FIG. 1 on a neck of a flask.

With additional reference to FIG. 9, the belt 180 may be used to secure the ribbon 100 to a vessel. While the vessel is shown as flask 20, the vessel may include, but not be limited to, a flask, a support stand, a bag, or a container. The belt 180 is threaded through the carrier portions 130 of the ribbon 100. The elongated body 182 of the belt 180 is disposed about a portion of flask 20 and passed through the channel 188 of the head 186. The organizer assembly 10 is then positioned on the flask 20 and the elongated body 182 is further pulled through the head 186 until the belt 180 is secured about the flask 20. As shown, the belt 180 is secured about a neck 22 of the flask 20 such that the ribbon 100 is positioned with the fingers 142 extending from the neck 22. The elongated body 182 may be trimmed at the head 186 to remove an excess length thereof.

When the ribbon 100 is secured to the flask 20 by the belt 180, the holders 144 of the ribbon 100 are substantially planar with one another and aligned such that each holder 144 is configured to receive a tube or conduit extending in a direction substantially orthogonal to the plane defined by the holders 144 of the ribbon. For example, as shown, the holders 144 of the ribbon 100 define a plane orthogonal to a central longitudinal axis of the flask 20 such that each holder 144 is configured to receive a tube or conduit exiting in a direction substantially parallel to the central longitudinal axis. In some embodiments, one or more holder 144 of a ribbon 100 may secure an adapter to the ribbon 100, e.g., adapter 200, 300, or 400.

The organizer assemblies detailed herein can be used to maintain a position of tubes or conduits relative to a vessel. The organizer assemblies detailed herein may be used to space tubes or conduits about a vessel, e.g., a neck of a flask, such that the tubes or conduits are separated from one another. The separation of tubes or conduits may improve identification of the tubes or conduits positioned about the vessel. Improved identification may increase efficiency and thus, decrease time required for a particular process which may result in cost savings and/or production increases.

Figure 10:
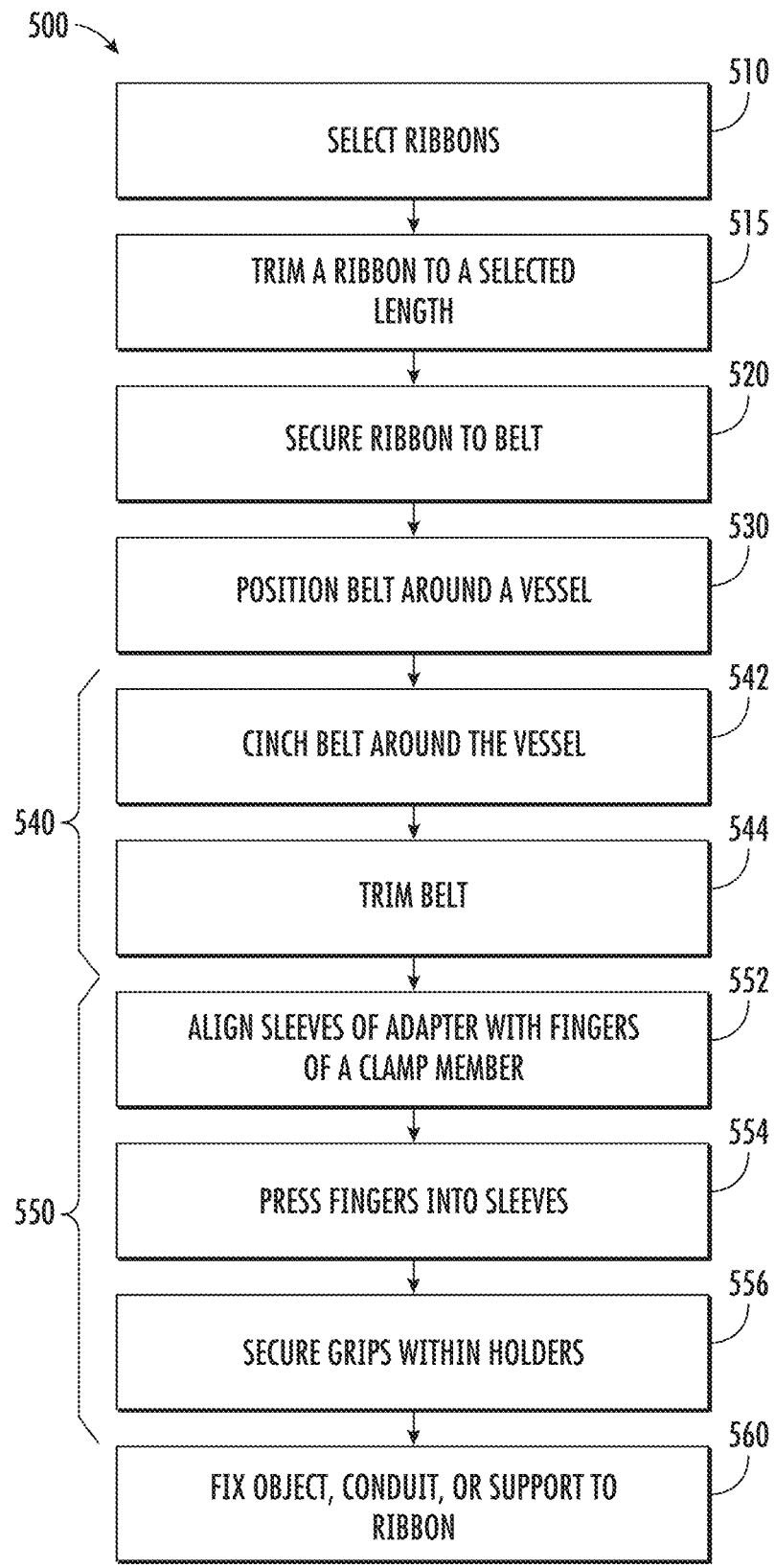
FIG. 10 is a flow chart of a method provided in accordance with an embodiment of the present disclosure.

With reference to FIG. 10, a method of securing an organizer assembly to a vessel is disclosed in accordance with the present disclosure and is referred to generally as method 500 with reference to the organizer assembly of FIGS. 1 and 2. The method 500 may be used to customize and secure an organizer assembly to a vessel. Once secured to the vessel, the method 500 may include disposing one or more conduits or objects in holders of the organizer assembly. In some embodiments, the method 500 may include securing an adapter to the organizer assembly before or after the organizer assembly is secured to the vessel.

The method 500 includes selecting one or more ribbons, e.g., ribbon 100, for the organizer assembly 10 (Step 510). The ribbons may be selected for the number of clamp members 120, the distance between clamp members 120, the size of holders 144 of the clamp members 120, and/or a central support axis passing through the holders 144 of the ribbon 100. Selecting the one or more ribbons may include trimming a ribbon to a selected length (Step 515). The selected length may be determined by an overall length of the ribbon or a number of clamp members 120. The ribbon 100 may be trimmed by severing a band 110 disposed between adjacent clamp members 120.

With the ribbon(s) 100 selected, an elongated body 182 of the belt 180 is passed through the carrier portions 130 of the selected ribbon(s) 100 to secure the ribbon(s) 100 to the belt 180 (Step 520). Specifically, the elongated body 182 is passed through the tunnels 132 of the carrier portions 130 with the teeth 184 of the elongated body 182 facing away from the ribbon 100. The method 500 may include orienting the ribbon(s) 100 with one another and the elongated body 182, such that the clamp portions 120 are oriented in a desired manner with the belt 180 as described below. In embodiments with more than one ribbon 100, the ribbons 100 may be ordered with one another before or during passing the elongated body 182 through the carrier portions (Step 518).

With the ribbon(s) 100 secured to the belt 180, the belt 180 with the ribbon(s) 100 is positioned on and around a portion of a vessel (Step 530). The portion of the vessel may be a neck 22 of a flask 20 as shown or may be a support, a tube, a conduit, container, or other vessel. The belt 180 may be positioned around the portion of the vessel with the ribbon(s) 100 aligned such that the clamp portions 120 are oriented relative to the vessel. The elongated body 182 is wrapped around the portion of the vessel and passed through the head 186 of the belt 180 to secure the ribbon 100 to the vessel (Process 540). When the elongated body 182 is passed through the head 186, the elongated body 182 passes through the channel 188 of the head 186 such that the teeth 189 of the elongated body 182 sequentially engage the pawl 189 to prevent the elongated body 182 from being retracted through the head 186. Specifically, the teeth 189 ratchet through the pawl 189 such that each tooth 189 defines a specific length of the elongated body 182. The elongated body 182 is passed through the head 186 until the belt 180 is cinched around the portion of the vessel (Step 542). When the belt 180 is cinched around the portion of the vessel, the belt 180 is taut about the portion of the vessel. When the belt 180 is taut, the carrier portions 130 may engage the portion of the vessel. The engagement of the carrier portions 130 with the portion of the vessel may maintain a position of the ribbon(s) 100 with respect to the vessel. With the belt 180 cinched around the portion of the vessel, the elongated body 182 may be trimmed at the head 186 to remove an excess portion of the body 182 extending beyond the head 186 (544).

The method 500 may include attaching an adapter 200 to a ribbon 100 (Process 550). The adapter 200 may be attached before or after the ribbon 100 is secured to the vessel. The adapter 200 may be selected to fix conduits or supports to the ribbon 100 that may not be receivable without the use of the adapter 200. For example, the adapter 200 may increase a number of holders, may provide holders of different sizes, may space the holders away from the ribbon 100 greater than the clamp portions 120 of the ribbon, or may secure objects in a different manner than possible with the holders of the ribbon 100. The adapter 200 is attached to the ribbon 100 by aligning the sleeves 267 of the adapter 200 with the fingers 242 of a clamp member 120 of the ribbon 100 (Step 552). With the sleeves 267 aligned with the fingers 142, the tips 243 of the fingers 142 are pressed into the sleeves 267 such that the fingers 142 are guided into the sleeves 267 (Step 554). As the fingers 142 are pressed into the sleeves 267, the grips 232 may urge the fingers 142 apart until the fingers 142 are fully disposed within the sleeves 267. As the fingers 142 are fully disposed into the sleeves 267, the tips 143 of the fingers 142 are disposed past the grips 232 such that the tips 143 move towards one another to secure the grips 232 within a holder 144 defined by the fingers 142 (Step 556). The fingers 142 may be formed of a material such that the fingers 142 are self-biased towards a neutral position such that when the fingers 142 are urged apart or together from the neutral position, the fingers self-biased back towards the neutral position. This self-biasing may maintain attachment of the adapter 200 to the clamp member 120. The adapter 200 may partially maintain attachment to the clamp member 200 by friction between the fingers 142 and the grips 232. As detailed above, the adapter 200 is attached to the ribbon 100. In some embodiments, other adapters 200, 300, or 400 may be attached in addition to or as an alternative to the adapter 200 as detailed above.

When the ribbon(s) 100 are secured to the vessel, a conduit or support may be fixed to the ribbon 100 (Step 560). The conduit or support may be fixed to the ribbon 100 by positioning the conduit or support within a holder 144 of the ribbon 100 or a holder 244 of an adapter 200. In certain embodiments, the conduit or support may be positioned in the holder 244 of an adapter 200 before the adapter 200 is attached to the ribbon 100. In particular embodiments, the conduit or support may be positioned in a holder 144 of the ribbon 100 before the ribbon 100 is secured to the vessel. The ribbon 100 may include one or more conduits and/or supports fixed to the ribbon 100. The ribbon 100 may allow for a plurality of conduits to be fixed about a vessel such as a flask, a tube, or a container. The fixing of the conduits about a vessel may organize the conduits within the laboratory environment. The organization of the conduits may prevent inadvertent contact with the conduits or other vessels. The organization of the conduits may aid in an ordered engagement with the conduits. For example, when sampling, the conduits may be selected in the order to which the conduits are fixed to the ribbon 100.

Figure 11:
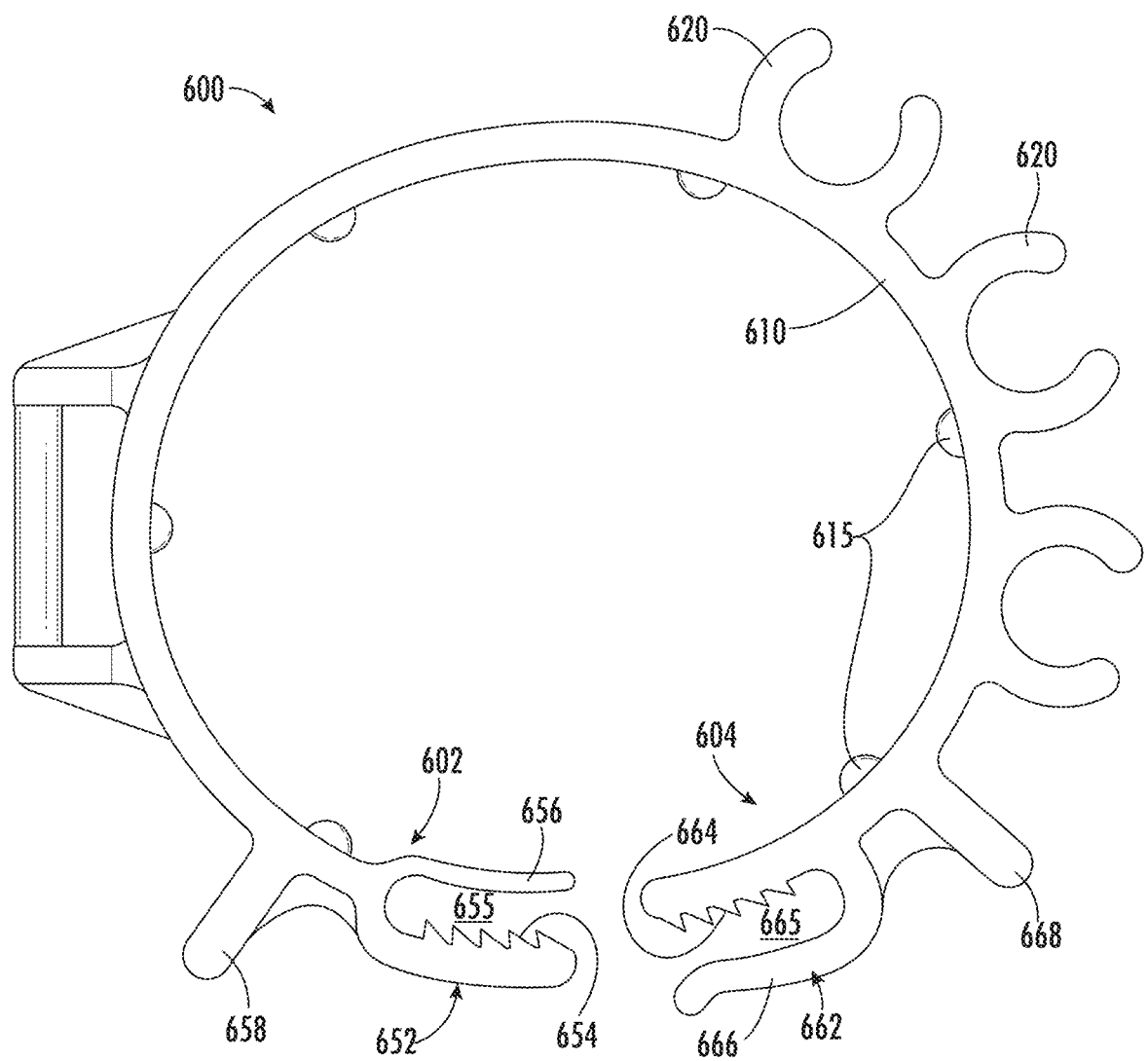
FIG. 11 is a plan view of another example tube organizer assembly provided in accordance with the present disclosure.

Referring now to FIG. 11, another ribbon is provided in accordance with an embodiment of the present disclosure and is referred to as ribbon 600. The ribbon 600 includes clamp members 620 that may be interconnected by a band 610. The band 610 aligns the clamp members 620 and spaces the clamp members 620 apart from one another. The clamp members 620 may be similar to the clamp members 120 detailed above. As such, the clamp members 620 will not be detailed herein for brevity. In some embodiments, the clamp members 620 may be used to fix one or more adapters e.g., adapter 200, 300, 400, to the ribbon 600. The ribbon 600 may be of monolithic construction. The ribbon 600 may be a molded or may be formed by additive manufacturing. The ribbon 600 may be formed of a variety of materials including, but not limited to, a polymeric material including thermosets or thermoplastics, a metal, or combinations thereof. The polymeric material may be a cross-linked polyurethane or a polyamide, e.g., silicone or nylon.

The band 610 may include protuberances 615 that extend from a surface of the band 610 opposite the clamp members 620. The protuberances 615 may be configured to contact a vessel when the ribbon 600 is secured thereabout. The protuberances 615 may space the ribbon from the vessel when the ribbon 600 is secured thereabout.

The ribbon 600 may include a closure assembly 650 that is configured to join end portions 602, 604 of the ribbon 600 such that the ribbon 600 forms a closed loop that can be secured about a vessel. The ribbon 600 includes a first end portion 602 and a second end portion 604 that is opposite the first end portion 602. The first end portion 602 includes a first closure 652 and the second end portion 604 includes a second closure 662. Each of the closures 652, 662 includes a rack 654, 664 that complement one another such that the racks 654, 664 are configured to secure the first end portion 602 and the second end portion 604 to one another in a plurality of positions.

The closures 652, 662 may include a retention arm 656, 666 that oppose the respective rack 654, 664 to define a receiver 655, 665 therebetween. The retention arm 656, 666 may engage a backside of the opposite rack 654, 664 when the opposite rack 654, 664 is received in the receiver 655, 665 to prevent the racks 654, 664 from disengaging with one another. The racks 654, 664 may ratchet over one another as the end portions 602, 604 are urged towards one another with the engagement of the racks 654, 664 with one another preventing separation of the end portions 602, 604. The end portions 602, 604 may include grips 658, 668 that provide a surface for the pressing the closures 652, 662 onto one another.

The ribbon 600 may be used in a manner similar to the ribbon 100 detailed above. In embodiments, the ribbon 600 may be secured about a vessel without a belt by engaging the first closure 652 with the second closure 662 to form a closed loop about the vessel. In some embodiments an organizer assembly includes the ribbon 600 and one or more adapters 200, 300, 400.

Figure 12:
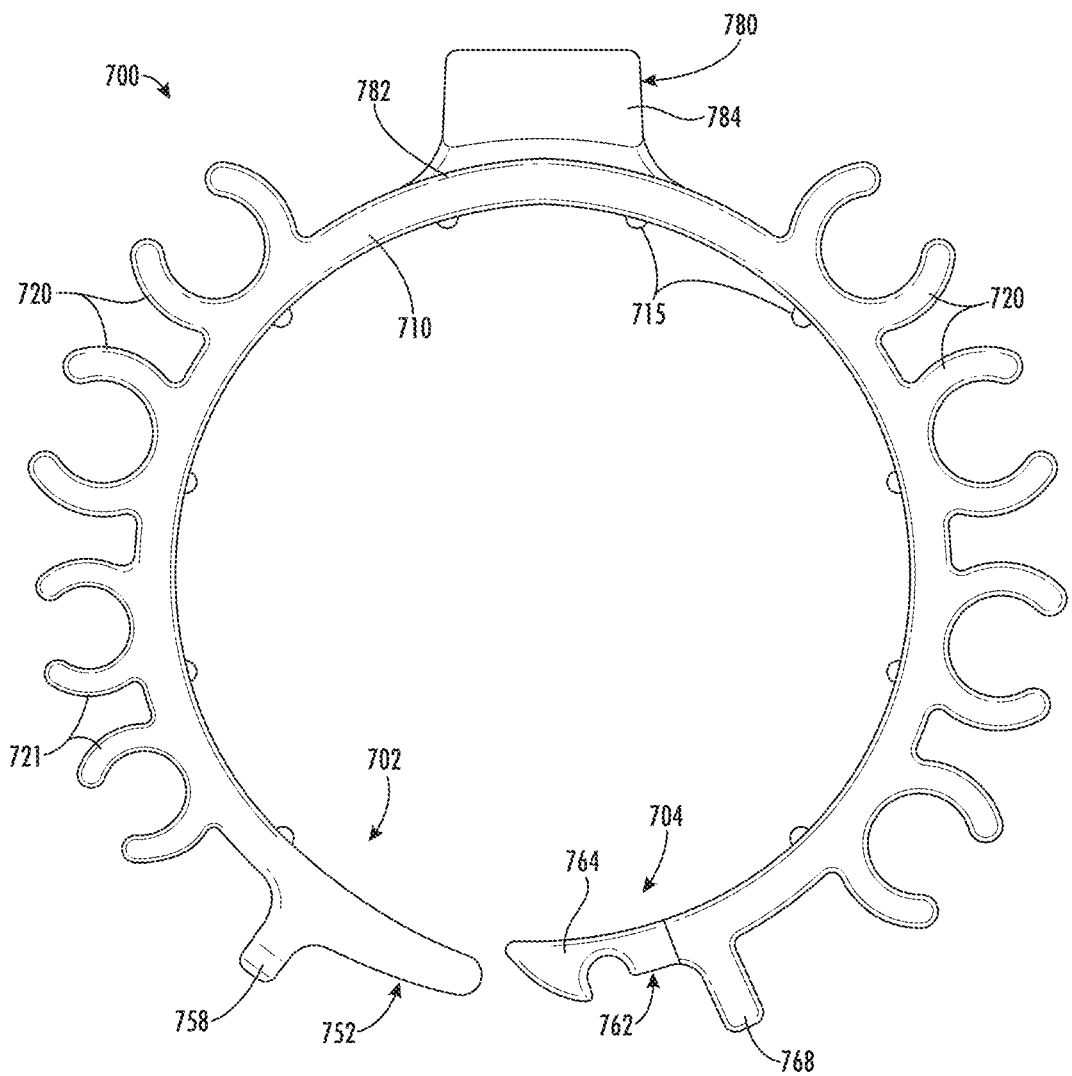
FIG. 12 is a plan view of another example tube organizer assembly provided in accordance with the present disclosure.
Figure 13:
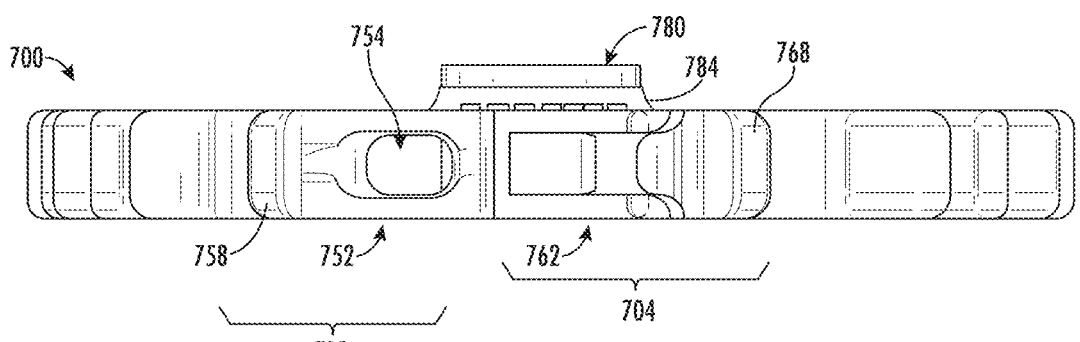
FIG. 13 is a front view of the tube organizer assembly of FIG. 12.

Referring now to FIGS. 12 and 13, another ribbon is provided in accordance with an embodiment of the present disclosure and is referred to as ribbon 700. The ribbon 700 includes first clamp members 720 that may be interconnected by a band 710. The ribbon 700 may include second clamp members 721 that are sized and dimensioned different from the first clamp members 720. The band 710 aligns the first clamp members 720 and the second clamp members 721 and spaces the first clamp members 720 and second clamp members 721 apart from one another along a length of the ribbon 700. The first clamp members 720 and the second clamp members 721 may be similar to the clamp members 120 detailed above. As such, the first clamp members 720 and the second clamp members 721 will not be detailed herein for brevity. In some embodiments, the first clamp members 720 or the second clamp members 721 may be used to fix one or more adapters e.g., adapter 200, 300, 400, to the ribbon 700 in a manner similar to the clamp members 120 detailed above.

The ribbon 700 may be a molded, machined, or may be formed by additive manufacturing. In embodiments, the ribbon 700 is of monolithic construction. The ribbon 700 may be formed of a variety of materials including, but not limited to, a polymeric material including a thermoset or a thermoplastic, a metal, or combinations thereof. The polymeric material may be a cross-linked polyurethane (e.g., silicone) or a polyamide (e.g., nylon).

The band 710 may include protuberances 715 that extend from a surface of the band 710 opposite the first clamp members 720. The protuberances 715 may be configured to contact a vessel when the ribbon 700 is secured thereabout. The protuberances 715 may space the ribbon from the vessel when the ribbon 700 is secured thereabout.

The ribbon 700 may include a closure assembly 750 that is configured to join end portions 702, 704 of the ribbon 700 such that the ribbon 700 forms a closed loop that can be secured about a vessel. The ribbon 700 includes a first end portion 702 and a second end portion 704 that is opposite the first end portion 702. The first end portion 702 includes a first closure 752 and the second end portion 704 includes a second closure 762. The first closure 752 may define a pocket 754 and the second closure 762 may include a hook 764. The pocket 754 sized and dimensioned to receive and retain the hook 764 when positioned therein such that the first end portion 702 and the second end portion 704 are secured to one another.

The end portions 702, 704 may include grips 758, 768 that provide a surface for the pressing the closures 752, 762 onto one another. In use, the grips 758, 768 may be used to position the hook 764 within the pocket 754 to secure the first end portion 702 to the second end portion 704.

In some embodiments, the ribbon 700 may include an adapter 780 disposed along the band 710. The adapter 780 may include a mount section 784 that is similar to the mount sections 240, 340, 440 of the adapters 200, 300, 400 respectively. The adapter 780 may include a receiver section 782 that is monolithically formed with the rest of the ribbon 700.

The ribbon 700 may be used in a manner similar to the ribbon 100 detailed above. In embodiments, the ribbon 700 may be secured about a vessel without a belt by engaging the first closure 752 with the second closure 762 to form a closed loop about the vessel. In some embodiments an organizer assembly includes the ribbon 700 and one or more adapters 200, 300, 400.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. An organizer comprising:
a ribbon extending a length, the ribbon comprising a clamp member extending from the ribbon at a position along the length of the ribbon, the clamp member including a pair of clamp fingers configured to selectively receive a conduit such that the conduit is fixed relative to the ribbon; and
an adapter comprising:
a receiver section having a pair of grips, the pair of grips configured to be received between the pair of clamp fingers of the clamp member with each grip of the pair of grips engaged by a respective clamp finger to secure the adapter to the clamp member; and
a mount section defining a passage, the passage configured to selectively receive the conduit such that the conduit is fixed relative to the ribbon.

2. The organizer according to claim 1, wherein each clamp finger of the pair of clamp fingers includes a rib extending therefrom, each rib defining at least one shelf with a respective clamp finger.

3. The organizer according to claim 2, wherein each grip of the pair of grips includes a ledge extending therefrom, each ledge received within the shelf of the respective clamp finger.

4. The organizer according to claim 1, wherein the receiver section of the adapter includes a bridge projecting between the pair of grips such that a pinch point is defined between the bridge and each grip of the pair of grips, each finger of the pair of fingers terminating in a tip received within a respective pinch point between adjacent the bridge.

5. The organizer according to claim 1, wherein the passage is configured to selectively receive the conduit substantially orthogonal to a holder defined by the pair of clamp fingers of the clamp member.

6. The organizer according to claim 1, wherein the mount section of the adapter includes a first wall and second wall opposite the first wall, the passage defined between the first wall and the second wall.

7. The organizer according to claim 6, wherein the first wall or the second wall includes an arcuate segment protruding therefrom such that a portion of the first wall or the second wall is closer to the opposing wall.

8. The organizer according to claim 7, wherein the arcuate segment is protruding from the first wall or the second wall such that a center of the first wall or the second wall is closer to the opposing wall.

9. The organizer according to claim 1, wherein the ribbon comprises another clamp member extending from the ribbon at another position along the length of the ribbon.

10. An organizer assembly comprising:
a belt having an elongated body; and
a ribbon extending a length and having a carrier side and a clamp side opposite the carrier side, the ribbon comprising:
a first clamp member extending from the clamp side of the ribbon at a first position along the length of the ribbon;
a first carrier portion extending from the carrier side of the ribbon at the first position, the first carrier portion defining a first closed tunnel, the first closed tunnel slidingly receiving the elongated body of the belt therethrough;
a second clamp member extending from the clamp side of the ribbon at a second position along the length of the ribbon;
a second carrier portion extending from the carrier side of the ribbon at the second position, the second carrier portion defining a second closed tunnel, the second closed tunnel slidingly receiving the elongated body of the belt therethrough such that the belt is parallel to the ribbon along the length of the ribbon;

a band connecting the first clamp member, the first carrier portion, the second clamp member, and the second carrier portion; and an adapter having a receiver section configured to be received by the first clamp member or the second clamp member such that the adapter is fixed relative to the ribbon, and a mount section defining a passage configured to selectively receive a conduit such that the conduit is fixed relative to the ribbon.

11. The organizer assembly according to claim 10, wherein the first clamp member and the second clamp member are configured to selectively receive a conduit such that the conduit is fixed relative to the ribbon.

12. The organizer assembly according to claim 11, wherein the receiver section of the adapter includes a pair of grips, the pair of grips configured to be received between the pair of clamp fingers of the first clamp member or the second clamp member with each grip of the pair of grips engaged by a respective clamp finger to secure the adapter to the first clamp member or the second clamp member.

13. The organizer assembly according to claim 10, wherein the band is configured to be severed transverse to the length of the ribbon.

14. The organize assembly according to claim 10, wherein the belt is parallel to the ribbon as it passes through the first closed tunnel and the second closed tunnel.

15. An organizer assembly comprising:
a belt having an elongated body; and
a ribbon extending a length and having a carrier side and a clamp side opposite the carrier side, the ribbon comprising:

a first clamp member extending from the clamp side of the ribbon at a first position along the length of the ribbon;

a first sidewall extending perpendicularly from the carrier side of the ribbon;

a second sidewall extending perpendicularly from the carrier side of the ribbon and parallel to the first sidewall;

a tunnel wall connecting the first sidewall and the second sidewall such that the first sidewall, the second sidewall, the tunnel wall, and the ribbon define a first closed tunnel therebetween, the elongated body of the belt slidingly received through the closed tunnel offset from and parallel to the length of the ribbon; and an adapter having a receiver section and a mount section, the receiver section comprising a pair of grips configured to be received by the first clamp member such that the adapter is retained to the ribbon, and the mount section, including a first pair of fingers and second pair of fingers, the first pair of fingers defining a first passage and the second pair of fingers defining a second passage, the first passage and the second passage each configured to receive a conduit therein.

16. The organizer assembly according to claim 15, wherein the first sidewall and the second sidewall extend from the carrier side of the ribbon at the first position.

17. The organizer assembly according to claim 15, wherein the first sidewall extends from the carrier side of the ribbon such that the first sidewall is coplanar with a first edge of the ribbon and the second sidewall extends from the carrier side of the ribbon such that the second sidewall is coplanar with a second edge of the ribbon opposite the first edge.

* * * * *